(12) United States Patent
Bebehani et al.

(10) Patent No.: US 6,415,174 B1
(45) Date of Patent: Jul. 2, 2002

(54) ECG DERIVED RESPIRATORY RHYTHMS FOR IMPROVED DIAGNOSIS OF SLEEP APNEA

(75) Inventors: Khosrow Bebehani, Arlington; John R. Burk, Aledo; Edgar A. Lucas, Fort Worth, all of TX (US)

(73) Assignee: Board of Regents the University of Texas System, Arlington, TX (US)

(*) Notice: Subject to any disclaimer, the term of this patent is extended or adjusted under 35 U.S.C. 154(b) by 0 days.

(21) Appl. No.: 09/434,503

(22) Filed: Nov. 5, 1999

Related U.S. Application Data

(60) Provisional application No. 60/107,564, filed on Nov. 9, 1998.

(51) Int. Cl.$^7$ .............................................. A61B 5/0402
(52) U.S. Cl. ......................................... 600/513; 600/512
(58) Field of Search ................................ 600/508, 509, 600/512, 517, 523

(56) References Cited

U.S. PATENT DOCUMENTS

| | | | |
|---|---|---|---|
| 5,203,343 A | 4/1993 | Axe et al. | 128/725 |
| 5,458,137 A | 10/1995 | Axe et al. | 128/204.23 |
| 5,645,069 A | * 7/1997 | Lee | |

OTHER PUBLICATIONS

F. Pinciroli, R. Rossi, L. Vergani, P. Carnevali, S. Mantero and O. Parigi, *Construction of Respiratory Waveforms*, Sep. 17, 1985, pp. 391–409.

F. Pinciroli, R. Rossi and L. Vergani, Detection of Electrical Axis Variation for the Extraction of Respiratory Information, 1985, IEEE, pp. 499–502.

George B. Moody, Roger G. Mark, Andrea Zoccola, and Sara Mantero, Derivation of Respiratory Signals from Multi-Lead ECGS, 1985 IEEE, pp. 113–116.

George B. Moody, Roger G. Mark, Marjorie A. Bump, Joseph S. Weinstein, Aaron D. Berman, Joseph E. Mietus, and Ary L. Goldberger, Clinical Validation of the ECG-Derived Respiration (EDR) Technique, 1987, IEEE, pp. 507–510.

S. S. Reisman and S. Yang, An Algorithm for Beat Detection and Classification in Exercise ECGS, 1987, IEEE, pp. 663–666.

A.M. Bianchi, U.J. Scholz, L.T. Mainardi, P. Orlandini, C. Pozza and S. Cerutti, Extraction of the Respiratory Influence From the Heart Rate Variability Signal by Means of Lattice Adaptive Filter.

(List continued on next page.)

*Primary Examiner*—Jeffrey R. Jastrzab
(74) *Attorney, Agent, or Firm*—Bracewell & Patterson, LLP

(57) ABSTRACT

Respiratory rhythms of a subject are derived from measured ECG signals utilizing leads placed for significant influence of chest movement on the ECG signals. The QRS pulses within ECG signals measured in two substantially orthogonal planes are located by applying a sequence of filters. The knot and period of the QRS pulses are then determined, with adjustments made during a learning phase of data sampling. The QRS pulse areas in both planes is then calculated. These pulse areas are employed to determine the angle of orientation of the depolarization wave's mean electrical axis (MEA) at the QRS pulse locations. Cubic spline interpolation of the data points for the MEA angle provides a smooth breathing curve, which may be scored for sleep disordered breathing events. The ECG-derived respiratory (EDR) signal may be employed in lieu of airflow measurements where such measurements are not available, or may be employed in conjunction with airflow measurements and/or measured cardiac activity data to discriminate between arrhythmias associated with disordered breathing versus those associated with cardiac malfunction, reducing misdiagnosis. The additional processing of ECG data required for derivation of respiratory rhythms may be easily automated and implemented at nominal incremental cost per unit.

19 Claims, 7 Drawing Sheets

OTHER PUBLICATIONS

Lingeng Zhao, Stanley Reisman and Thomas Findley, Respiration Derived from the Electrocardiogram During Heart Rate Variability Studies.

David Caggiano and Stanley Reisman, Respiration Derived from the Electrocardiogram: A Quantitative Comparison of Three Different Methods, 1996, IEEE, pp. 103–104.

Prameela Ray, An Investigation of Respiratory Signal Derived from Electrocardiography Signals for Detection of Sleep Apnea, The University of Texas at Arlington, Dec. 1996.

* cited by examiner

ECG DERIVED RESPIRATORY RHYTHMS FOR IMPROVED DIAGNOSIS OF SLEEP APNEA

This application claims priority from provisional application Ser. No. 60/107,564, filed Nov. 9, 1998.

BACKGROUND OF THE INVENTION

1. Technical Field

The present invention relates generally to diagnosis of sleep disordered breathing and in particular to diagnosis of sleep disordered breathing utilizing electrocardiographic measurements. Still more particularly, the present invention relates to derivation of respiratory data from electrocardiographic measurements for determining either the presence of sleep disordered breathing causing or aggravating cardiac symptoms or the absence of sleep disordered breathing influence on cardiac symptoms due to cardiac pathology.

2. Description of the Related Art

Sleep disordered breathing is a significant problem for a large portion of the population. Sleep apnea, an intrinsic dyssomnia involving cessation of breathing during sleep and resulting in complete or partial arousal from sleep, is one of the most prevalent forms of sleep disordered breathing. Symptoms of the disorder include daytime sleepiness, fatigue or tiredness, and irritability, which may seriously impair the performance of the individual.

Sleep apnea is typically defined as the cessation of air exchange (breathing) from the nostrils or mouth lasting at least 10 seconds. Partial or complete arousal from sleep is considered a defensive mechanism most likely stimulated by rising carbon dioxide levels in the blood during the apneic event to reestablish ventilation and prevent death in the sleeping subject. Three established categorized of sleep apnea include: obstructive sleep apnea, obstruction of the upper airway; central sleep apnea, cessation of ventilatory effort; and mixed apnea, a combination of both upper airway obstruction and cessation of ventilatory effort.

Sleep disordered breathing may also take the form of a decrease in ventilation during sleep rather than a complete sleep apnea, which may result in hypercarpnea and sleep disturbance and is classified as hypopnea. Apneic events are usually quantified (or "scored") as either (1) more than 75% reduction in air flow, with or without change in oxygen saturation in the blood ($SpO_2$), or (2) more than 50% reduction in air flow combined with a decrease of blood oxygen saturation by more than 10%. Hypopneic events may be variously quantified as: (1) either a 50% or greater reduction in air flow combined with at least a 4% reduction in blood oxygen saturation or, alternatively, a 20%–50% reduction in airflow in association with at least 2% loss of blood oxygen saturation; (2) a 50% or greater reduction in thoracic and abdominal activity; (3) a change in electromyogram (EMG) measurements accompanied by, rolling eye movements, indicating arousal; and/or (4) a change in electroencephalogram (EEG) measurements combined with a 20% decrease in air flow, independent of decrease in blood oxygen saturation.

While the distinction between apnea and hypopnea is largely one of severity, sleep disordered breathing diagnosis may entail measurement of both types of events. For example, the apnea-hypopnea index (AHI), representing a number of either apneic or hypopneic events per hour for a subject, is more commonly used than the apnea index (AI), representing only the total number of apneic events per hour for the subject. An AHI of more than 5 events per hour, regardless of severity, is usually qualified as sleep apnea. Other variables such as average duration of an event, number of apneic versus hypopneic events, and average decrease in blood oxygen saturation during events are utilized to determine the severity of the disorder.

Polygraphic monitoring, or polysomnography, the measurement of vital body signals during sleep, is the most commonly employed method of diagnosing sleep disorders, including sleep apnea. The data is collected during the patient's normal sleeping time and is later scored (evaluated) visually. Various signals are recorded during the night to identify different sleep stages, respiratory variables, heart function, and muscle tone, all of which aid in scoring sleep disordered breathing events.

A conventional arrangement of the polygraphic monitoring instrumentation employed is depicted in FIG. 8. A polygraphic monitoring unit 802 is connected by a plurality of leads 804 to sensors attached to patient 806. Polygraphic monitoring unit 802 is capable of measuring a variety of body functions: electroencephalogram (EEG) lead 804a is employed to measure electrical brain activity; electrooculogram (EOG) lead 804b is employed to detect eye movements; airflow lead or leads 804c are employed to measure air flow signals from as many as three thermistors placed near the patient's nostrils and mouth; electromyogram (EMG) lead 804d is employed to measure muscle tone from the patient's chin area; electrocardiogram (ECG) leads 804e are employed to measure the heart function; and chest and abdominal band leads 804f and 804g are employed to measure thoracic and abdominal movements, respectively. Additionally, a pulse oximeter (not shown) may be employed to record blood oxygen saturation, an electrode may be placed on the tibialis anterior to monitor leg muscle activity, and a video recording of the patient may be taken utilizing infrared low light technology.

Measurements taken from polygraphic monitoring unit 802 are typically filtered and amplified, and recorded on a data acquisition system 808 such as those available from Tele-factor Corporation of West Conshohocken, Pa. The polysomnography signals are also usually digitized by an analog-to-digital converter 810 and transmitted to a data processing system 812 for processing and/or storage. Converter 810 may, for example, be a DAS 1200 series A/D converter board, available from Keithly Instruments, Inc. of Massachusetts, within data processing system 812.

Conventional polygraphic monitoring instrumentation is often uncomfortable to the patient. The instrumentation also embraces several forms of respiration monitoring. Currently, two broad categories of respiration monitoring may be identified: direct methods, such as nasal thermistors, spirometers, and pneumotachometers, measure air flow in and out of the lungs; indirect methods, which presently include whole body plethysmographs, inductance and impedance plethysmographs, and strain gauge measurement of chest and abdomen circumference, measure effects of respiration on the body. While direct methods are most accurate, they generally interfere with normal respiration. Most indirect methods, on the other hand, either lose their calibration readily or immobilize the patient (e.g., whole body plethysmograph).

Sleep disordered breathing is prevalent in individuals suffering from cardiovascular disease. ECG signals are routinely recorded in studies for patients with cardiac problems, as well as in patients having respiratory disorders, sleep disorders, and patients in intensive care units. ECG signals are therefore readily available for patients having a variety of disorders. Furthermore, millions of patients are screened each year using extended ECG monitoring (at least 24 hours), while generally their respiration is not monitoring due to the added cost and inconvenience of conventional airflow monitoring equipment.

Advances in the field of electrocardiography have rendered analysis and conditioning or ECG signals robust. Measurement of ECG signals does not interfere with normal breathing. Established technology has existed for years for measurement of the ECG in ambulatory patients. Thus, measurement of ECG signals is more comfortable and less intrusive for the patient than polygraphic monitoring. Properly attached ECG leads are less prone to error due to patient movement.

It is well-known that respiration affects ECG signals, principally as a result of chest movement. Much work has been performed to eliminate this effect from ECG signals to enhance detection of arrhythmia. Capture of chest movement induced modulation of ECG signals, however, could provide a means for extracting respiratory rhythms from ECG signals.

Derivation of respiratory rhythms from ECG signals would not require supplementary sensors. ECG-derived respiratory (EDR) signals could also provide valuable clinical information if they reveal an association between abnormal respiratory and cardiac events. Presently, however, no ECG monitoring device provides information regarding the patient's breathing function. Thus, respiratory influence on cardiac function is not available to the attending physician when making an ECG-based diagnosis.

It would be desirable, therefore, to provide a mechanism for deriving respiratory data from ECG measurements. It would further be advantageous if the mechanism for generating EDR signals could be implemented in connection with a variety of mechanisms utilize to diagnose cardiac, respiratory, or sleep disorders.

SUMMARY OF THE INVENTION

Respiratory rhythms of a subject are derived from measured ECG signals utilizing leads placed for significant influence of chest movement on the ECG signals. The QRS pulses within ECG signals measured in two substantially orthogonal planes are located by applying a sequence of filters. The knot and period of the QRS pulses are then determined, with adjustments made during a learning phase of data sampling. The QRS pulse areas in both planes is then calculated. These pulse areas are employed to determine the angle of orientation of the depolarization wave's mean electrical axis (MEA) at the QRS pulse locations. Cubic spline interpolation of the data points for the MEA angle provides a smooth breathing curve, which may be scored for sleep disordered breathing events. The ECG-derived respiratory (EDR) signal may be employed in lieu of airflow a measurements where such measurements are not available, or may be employed in conjunction with airflow measurements and/or measured cardiac activity data to discriminate between arrhythmias associated with disordered breathing versus those associated with cardiac malfunction, reducing misdiagnosis. The additional processing of ECG data required for derivation of respiratory rhythms may be easily automated and implemented at nominal incremental cost per unit.

BRIEF DESCRIPTION OF THE DRAWINGS

The novel features believed characteristic of the invention are set forth in the appended claims. The invention itself, however, as well as a preferred mode of use, further objectives and advantages thereof, will best be understood by reference to the following detailed description of an illustrative embodiment when read in conjunction with the accompanying drawings, wherein:

DETAILED DESCRIPTION

Figure 1:
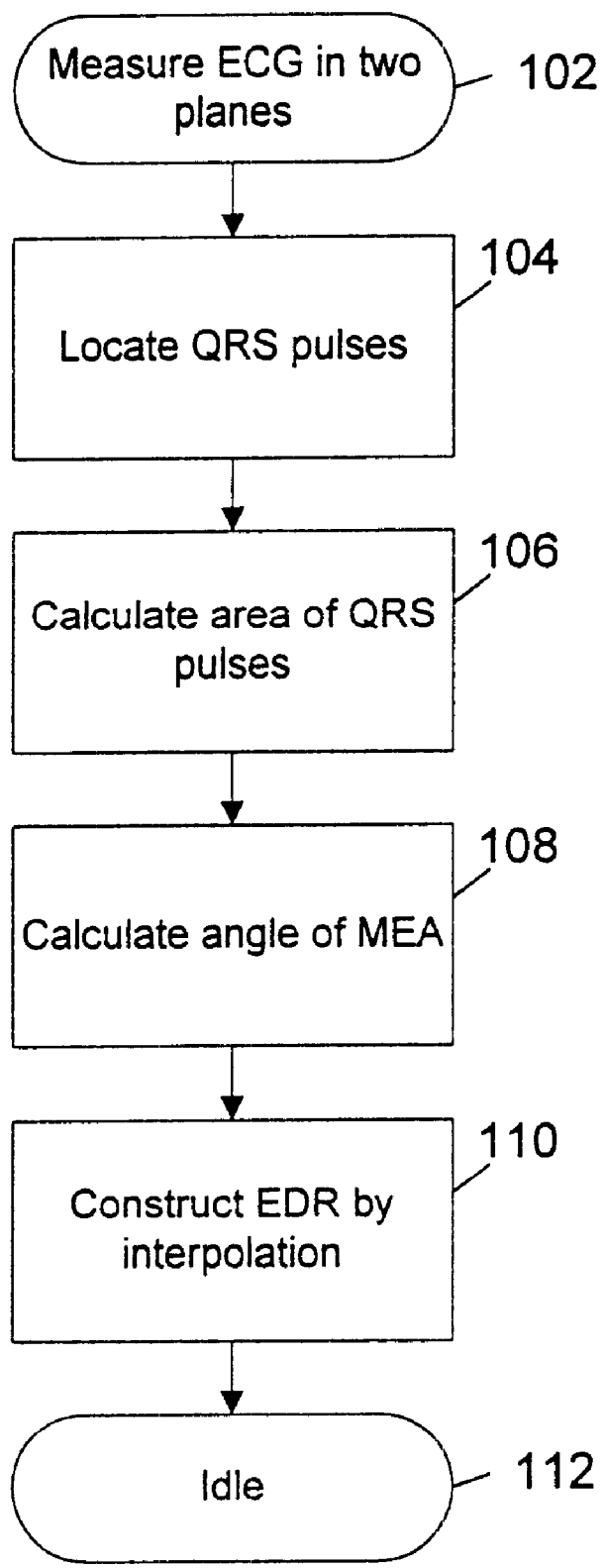
FIG. 1 depicts a high level flowchart for a process of deriving respiratory rhythms from ECG signals in accordance with a preferred embodiment of the present invention.

With reference now to the figures, and in particular with reference to FIG. 1, a high level flowchart for a process of deriving respiratory rhythms from ECG signals in accordance with a preferred embodiment, of the present invention is depicted. The process begins at step 102, which depicts receiving ECG measurement data taken from two measurement planes utilizing leads between selectively placed transducer electrodes attached to the patient.

Derivation of respiratory rhythms from ECG signals depends on how the ECG signal components are measured. The usefulness of ECG signal component measurements in deriving respiratory rhythms may be maximized by careful placement of the leads, taking into account the patient's position (i.e., erect or supine).

Figure 2A:
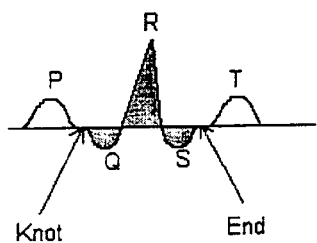
FIGS. 2A–2C are diagrams of ECG signals and their components, their projections onto various measurement planes, and the components of measured ECG signals.
Figure 2C:
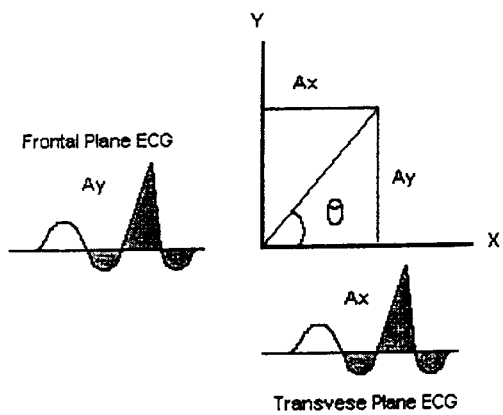
Figure 2B:
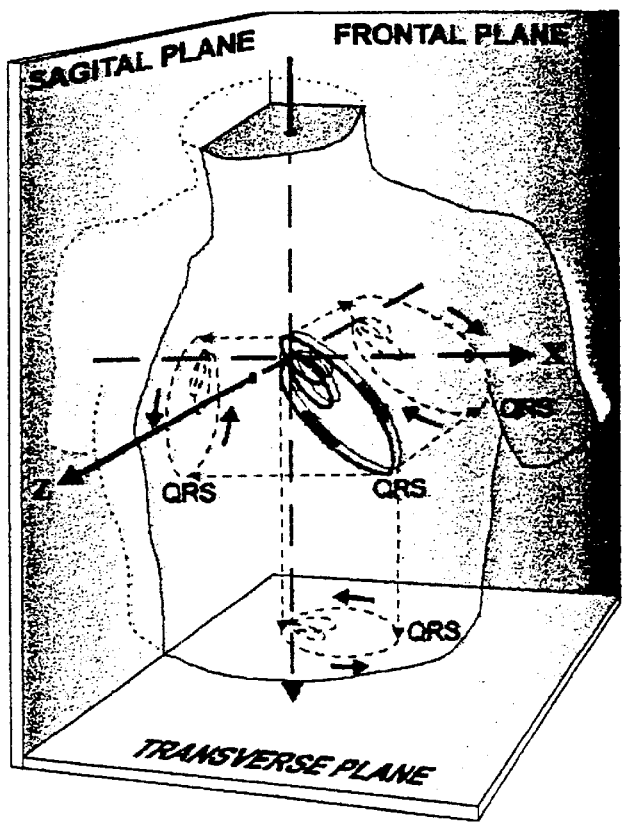

Referring to FIGS. 2A–2C, diagrams of ECG signals and their components, their projections onto various measurement planes, and the components of measured. ECG signals are illustrated. Electrocardiography is based on the principle that current flow in the extracellular fluid is proportional to the rate of change of action potential in the myocardial cells of the heart. A plateau in the action potential, produces a negligible current in the extracellular fluid, while repolarization and depolarization produce high currents.

The mechanism of electrical conductivity in the body involves ionic currents (ions as charge carriers). Bipotential body surface electrodes employed in electrocardiography transduce those ionic currents into electric currents, making it possible to record the bioelectric activity of the heart. Repolarization and depolarization in the myocardium may thus be seen as discrete events in the electrical signal transduced by these surface electrodes placed on the thorax. A recording of the electrical signal is referred to as an electrocardiogram.

ECG signals are conventionally characterized as including the P-, Q-, R-, and S-wave components illustrated in FIG. 2A. These components correspond to movement of the depolarization wave through the heart, causing contraction. The area of the QRS complex within the ECG signal is typically a factor of interest.

In a normal heart, the total cycle of the PQRS (depolarization wave) starts at the SA node (generator) and travels away from that node through parts of the atria, causing the P-wave. Next, the AV node receives impulses from the SA node and also from the sympathetic and parasympathetic nervous system.

After passing through the AV node, the depolarization wave spread rapidly along the ventricular septum and to the left and right ventricles, thus causing a contraction. The QRS complex of interest in the present invention is recorded during this phase of rapid ventricular depolarization. The path of the depolarization wave around the heart is illustrated in FIG. 2B. In the intact heart, the instantaneous depolarization vector changes continuously as the depolarization wave flows through the heart. The vectorial sum of all instantaneous vectors is referred to as the mean electrical axis (MEA).

The direction of the flow of the depolarization wave in three dimensional space gives the direction of the MEA. As illustrated in FIG. 2B, projections of the depolarization wave path may be measured in various planes: the frontal (x-y) plane, the transverse (x-z) plane, and the sagittal (y-z) plane (where the x axis is oriented across the front of the patient's body and the y axis is oriented along the length of the patient's body). The position of the electrodes on the thorax determines the polarity and amplitude of the ECG events; that is, the position of the leads determine the plane in which the depolarization wave signal is measured.

In practice, x and y axis leads are utilized to find the orientation of the MEA in two dimensions, along the frontal and transverse planes as illustrated in FIG. 2C. Data is not normally collected along the sagittal plane for routine ECG monitoring. The area of the QRS complex in the frontal plane ($A_y$) and the area of the QRS complex in the transverse plane ($A_x$) are then utilized to determine the orientation ($\theta$) of the MEA in the x-y plane.

Figure 3:
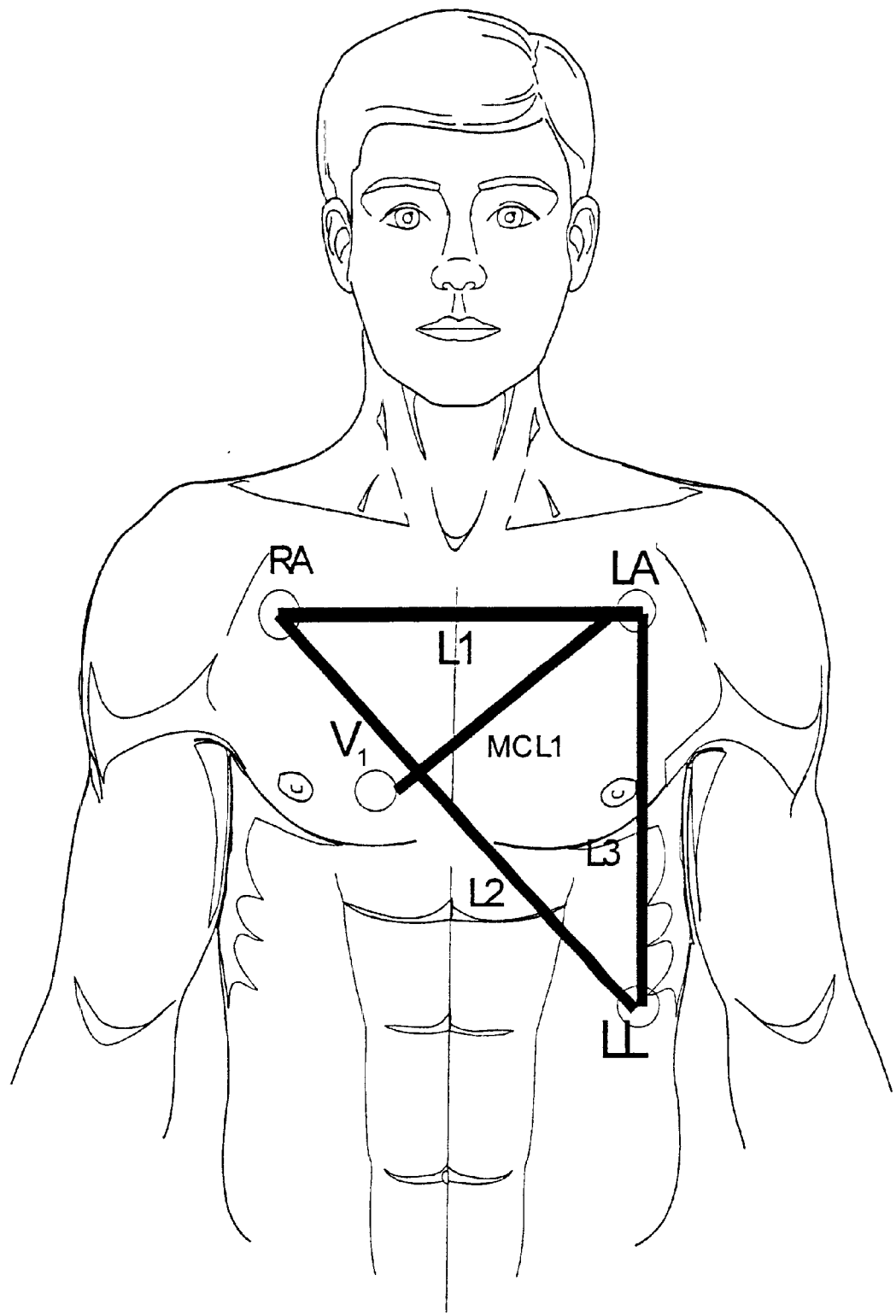
FIG. 3 depicts a diagram of electrode placement for ECG measurement in deriving respiratory rhythms from ECG signals in accordance with a preferred embodiment of the present invention.

Referring now to FIG. 3, a diagram of electrode placement for ECG measurement in deriving respiratory rhythms from ECG signals in accordance with a preferred embodiment of the present invention is depicted. Respiration affects ECG signals both through a low frequency baseline shift, which is routinely filtered as baseline noise, and by amplitude modulation of the QRS pulses, primarily due to chest movement, which changes the position of the leads relative to the heart. Amplitude modulation of QRS pulse measurements results in a change of the area of the QRS pulses measured in different planes.

Leads L1, L2, and L3 depicted in FIG. 3 are three standard frontal plane bipolar leads (vectors) measured from electrodes placed on the patient's thorax as shown. With some individual variation due to heart orientation and conductivity/resistivity, the orientation of the MEA in the frontal plane is normally along lead L2, which therefore records the largest signal amplitude. A modified L2 lead, which employs only positive and negative electrodes (RA and LL) rather than standard positive, negative, and reference electrodes (RA, LL and LA), is preferably employed in the present invention.

Normally, an electrode is also placed on the patient's back to obtain transverse plane measurements. Since the back electrode can be uncomfortable for the patient and noisy due to patient movement, a modified transverse plane lead $MCL_1$ is preferably employed in the present invention to make horizontal plane measurements. Electrode $V_1$, placed at the fourth intercostal space to the right of the sternum, is utilized as one electrode for lead $MCL_1$, while electrode LA close to the upper left arm is utilized as the second electrode. Only the relative amplitude of the resultant ECG signal changes. Measurements from leads L2 and $MCL_1$ thus provide components of the area of the QRS complex in two orthogonal planes, with lead L2 preferably designated for measuring $A_y$ and lead $MCL_1$ designated for measuring $A_x$.

In erect patients, expansion and contraction of the chest during respiration takes place in both the horizontal (within the transverse plane due to expansion and contraction of the chest) and vertical (within the frontal plane due to diaphragmatic movement) directions. Diaphragmatic activity and the intercostal muscles cause expansion and contraction in three dimensional space, a periodic or a periodic movement which effects the ECG signals in each lead differently. Thus, for erect patients, lead L1 will be most effected by the horizontal component of chest movement during respiration and lead L3 will be most affected by the vertical component of thoracic movement, while lead L2 will be least affected. Thus, for an erect patient, the respiratory signal may be derived from measurement on lead L1 of $A_x$, the horizontal area component of the QRS pulse, and on lead L3 of $A_y$, the vertical area component.

The derivation of the EDR signal from ECG measurements is the same for either pair of leads—L1 and L3 or modified L2 and $MCL_1$—and may be applied separately to both pairs of leads. ECG signals are preferably sampled from the selected lead pair at 500 Hz.

Referring again to FIG. 1, upon receiving ECG measurements from a selected lead pair as depicted in step 102, the process passes to step 104, which illustrate locating QRS pulses within the measured ECG data. To be able to calculate the area of the QRS complex, it is necessary to have a robust process for accurately detecting the correct location of the QRS complex even under noisy conditions. A number of QRS detection algorithms are known in the art. However, the process of QRS location detection in the present invention has a high accuracy of detection and low noise sensitivity, resulting in fewer false positives and fewer false negatives.

Figure 4:
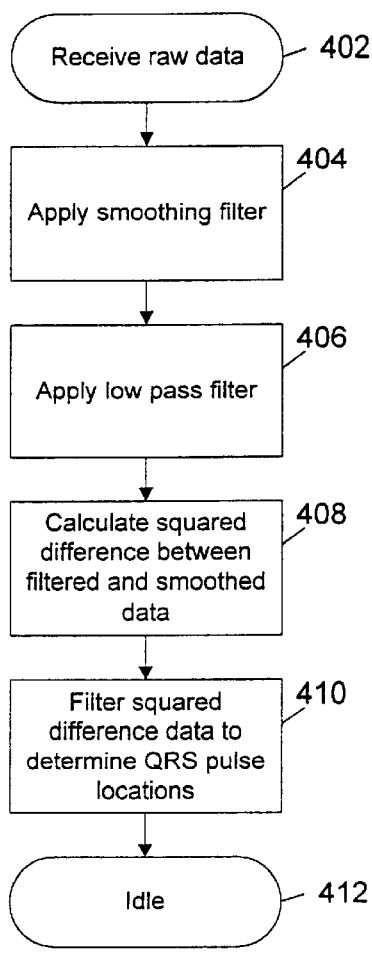
FIG. 4 is a high level flowchart for a process of detecting QRS pulse locations within measured data from an ECG signal in accordance with a preferred embodiment of the present invention.
Figure 5A:
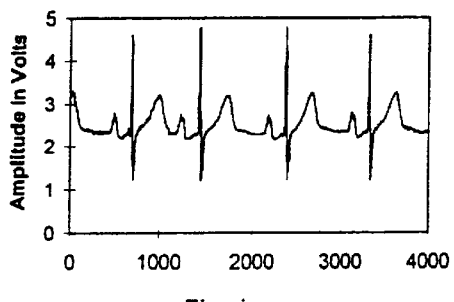
FIGS. 5A–5E are data plots for a process of detecting QRS pulse locations within measured data in accordance with a preferred embodiment of the present invention.

Referring to FIGS. 4 and 5A–5E, which are intended to be considered together, a high level flowchart and corresponding data plots for a process of detecting QRS pulse locations within measured data in accordance with a preferred embodiment of the present invention are illustrated. The process depicted in FIG. 4 begins at step 402, which depicts receiving raw ECG data from which QRS pulse locations are to be determined. A data plot of suitable raw data X, representing (possibly amplified) measurements of the amplitude an ECG signal in volts as a function of time, is shown in FIG. 5A.

Figure 5B:
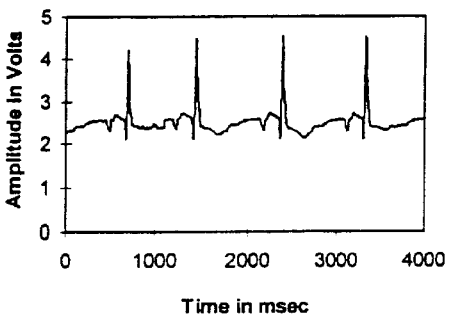

The process of FIG. 4 then passes to step 404, which illustrates applying a smoothing filter to reduce noise. A suitable smoothing filter may be emulated by calculating:

$$Y1(n) = \frac{X(n-1) + 2X(n) + X(n+1)}{4} \tag{1}$$

where Y1 represents the smoothed data. The data plot shown in FIG. 5A smoothed using the filter modeled by equation (1) is shown in FIG. 5B.

Figure 5C:
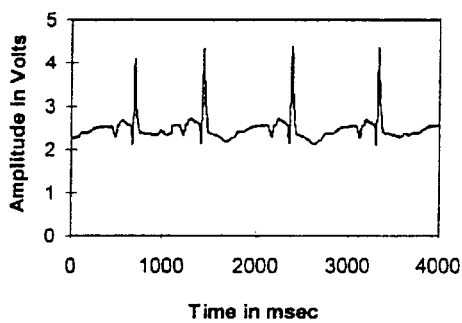

From step 404, the process of FIG. 4 next passes to step 406, which depicts applying a low pass filter to the smoothed data, modeled by the computation of:

$$Y2(n) = \frac{1}{2m+1}\sum_{k=n-m}^{n+m} Y1(k) \qquad (2)$$

where Y2 represents the low pass filtered data and m=2. A data plot of the smoothed data in FIG. 5B after a low pass filter is applied as described is shown in FIG. 5C.

Figure 5D:
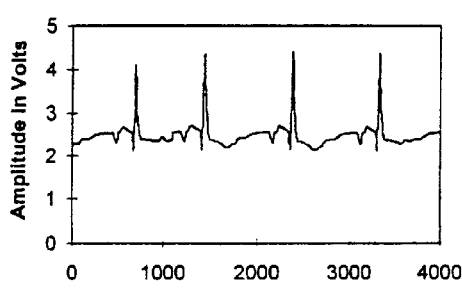

From step 406, the process of FIG. 4 then passes to step 408, which illustrates computing a squared difference between the smoothed data resulting from step 404 and the low pass filtered, smoothed data resulting from step 406. The squared difference is computed by:

$$Y3(n)=(Y1(n)-Y2(n))^2 \qquad (3)$$

where Y3 represents the computed squared difference. A data plot for the squared difference between the smoothed data in FIG. 5B and the low pass filtered, smoothed data shown in FIG. 5C is shown in FIG. 5D. Sharp peaks corresponding to the location of QRS pulses appear after calculating the squared difference, because the squared difference between Y1 and Y2 enhances the high frequency components present in the QRS pulse while removing the lower frequency components.

Figure 5E:
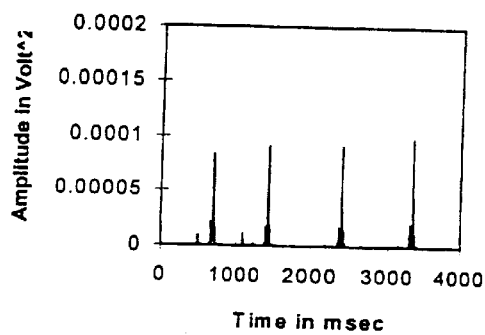

From step 408, the process of FIG. 4 next passes to step 410, which depicts low pass filtering the squared difference data again to cut off higher frequencies, utilizing a filter which may be modelled by:

$$Y4(n) = \frac{1}{(2m+1)64}\sum_{k=n-m}^{n+m} Y3(k) \qquad (4)$$

where Y4 represents the low pass filtered, squared difference data signal and m=2 is again selected. A plot of the data in FIG. 5D which has been low passed filtered with equation (4) is shown in FIG. 5E. The locations of the peaks in this filtered signal Y4 represent the actual QRS pulse locations. An array of pulse location may thus be generated for further processing efforts.

Referring once again to FIG. 1, from step 104 the process next passes to step 106, which depicts calculating the area of the QRS pulses which have been located within the raw ECG data. For this step, the R-wave component of each QRS pulse within the ECG signal is first located by searching for it in the vicinity of the detected QRS pulse location. Once the R-wave component is identified, the position of the knot (start) and end of the QRS pulse are established. The knot and end positions within the QRS pulse may be identified utilizing suitable zero-crossing detection algorithms known in the art.

The position of the knot, and thus the area of the QRS pulse, varies to a small extent from subject to subject. Accordingly, the first twelve seconds worth of raw ECG data is utilized as a "learning phase" to adjust the knot position and period of the QRS pulse for a particular subject, which are then utilized in computing the area of the QRS pulse. The twelve second learning phase period was selected by trial and error, determined to be sufficiently long to ascertain the subject-specific knot position and pulse period to an acceptable accuracy.

By trial and error, the knot is placed between 40 to 60 msec before the R-wave component of each QRS pulse during the learning phase. The area of each QRS pulse is calculated starting from the knot over the next approximately 100 to 150 msec, a period which is adjusted during the learning depending on the subject-specific period of the QRS pulse. The area of the digitized QRS pulse data may be calculated to a reasonable approximation by computing the sum of the areas of rectangles represented by the sample period and each sample value within the QRS pulse period. The area of the QRS pulse is separately calculated for each lead within a selected pair (L1 and L3 or modified L2 and MCL$_1$), and the location of the QRS pulse for data measured from each lead is noted.

The process then passes to step 108, which illustrates calculating the angle of the mean electrical axis for each QRS pulse from:

$$\theta_{MEA} = \tan^{-1}\frac{A_y}{A_x} \qquad (5)$$

where $\theta_{MEA}$ (or simply $\theta$) is the angle of orientation of the MEA, $A_x$ is the corresponding QRS pulse area as calculated from the measurements taken on one lead (L1 or MCL$_1$), and $A_y$ is the corresponding QRS pulse area as calculated from the measurements taken on the other lead (L3 or modified L2). The MEA orientation values are then stored in association with the location of the QRS pulse.

The process, next passes to step 110, which depicts construction of the ECG-derived respiratory (EDR) signal by interpolation between consecutive values of the MEA orientation. A cubic spline interpolation is suitable for generating the EDR signal from the computed MEA orientation data points, generating a smooth breath signal.

Cubic spline interpolation, a technique known in the art, utilizes three consecutive original data points to calculate the coefficients in a cubic equation for a curve passing through those points. The resulting cubic equation is then employed to generate additional data points between the original data points. Thus a series of cubic equations, each having (potentially) different coefficients, is utilized to interpolate the MEA orientation data derived from the raw ECG signals described above.

The cubic equation, obtained by taking the first four terms of the Maclaurin series, is represented as:

$$\theta_k(t) = \theta_k'''(0)\frac{t^3}{3} + \theta_k''(0)\frac{t^2}{2} + \theta_k'(0)t + \theta_k(0) \qquad (6)$$

where t is time, $\theta_k$ (0) is the initial value coefficient, $\theta_k'(0)$ is the first differential coefficient, $\theta_k''(0)$ is the second differential coefficient, and $\theta_k'''(0)$ is the third is differential coefficient of the cubic equation represented by $\theta_k$ (t). Equation (6) may be differentiated to obtain:

$$\theta_k'(t)=\theta_k'''(0)t^2+\theta_k''(0)t+\theta_k'(0). \qquad (7)$$

If $\theta_k$, $\theta_{k+1}$, and $\theta_{k+2}$ are three points obtained by calculating the angle of MEA and T$_1$ is the time between $\theta_k$ and $\theta_{k+1}$ while T$_2$ is the time between $\theta_{k-1}$ and $\theta_{k+2}$, then by assuming that at t=0, $\theta_k(0)=\theta_k$ and $\theta_k'(0)=\theta_k'=(\theta_{k+1}-\theta_k)/T_1$ and forcing the equation to pass through $\theta_{k+1}$, at t=T$_1$, $\theta_k(T_1)=\theta_{k+1}$. The first differential may be written as $\theta_k'(T_1)=(\theta_{k+2}-\theta_k)/T_2$.

From equation (6) at t=T₁ we obtain $$\theta_{k+1} = \theta_k'''(0)\frac{T_1^3}{3} + \theta_k''(0)\frac{T_1^2}{2} + \theta_k'(0)T_1 + \theta_k(0) \quad (8)$$

and at t=T₂ we obtain $$\theta_{k+2} = \theta_k'''(0)\frac{T_2^3}{3} + \theta_k''(0)\frac{T_2^2}{2} + \theta_k'(0)T_2 + \theta_k(0). \quad (9)$$

Therefore, from equations (8) and (9):

$$\theta_k''(0) = -6\frac{(\theta_k - \theta_{k+1})}{T_1^2} - 2\left(\frac{2\theta_k' + \frac{(\theta_{k+2} - \theta_k)}{T_2}}{T_1}\right) \quad (10)$$

and $$\theta_k'''(0) = 12\frac{(\theta_k - \theta_{k+1})}{T_1^3} + 6\left(\frac{\theta_k' + \frac{(\theta_{k+2} - \theta_k)}{T_2}}{T_1^2}\right). \quad (11)$$

If there are 0 to n number of points in the signal to be interpolated, then k varies from 0 to n−2 and k number of equations are generated.

The cubic spline interpolation technique described above may be utilized to represent the EDR signal with a sampling rate of 10 Hz. The process then passes to step 112, which illustrates the process becoming idle until subsequent ECG data is provided for derivation of respiratory rhythms in accordance with the present invention. The EDR signal may then be visually scored as a respiratory signal for apneic and hypopneic events in accordance with the known art, or evaluated utilizing different methods.

Figure 6A:
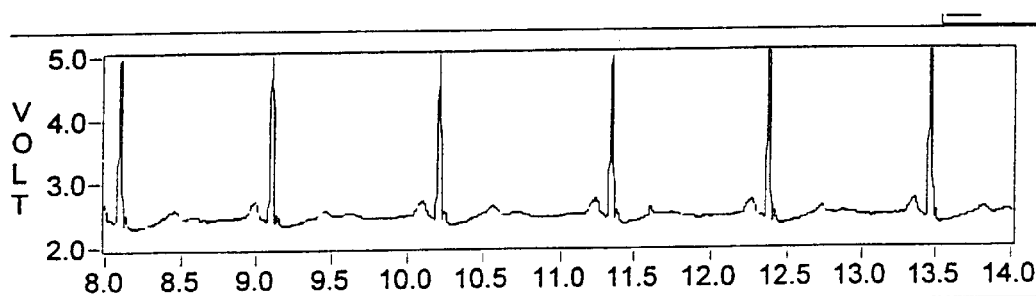
FIGS. 6A–6D depict data plots for measured and derived data utilizing the process for derivation of respiratory rhythms from ECG signals in accordance with a preferred embodiment of the present invention.
Figure 6B:
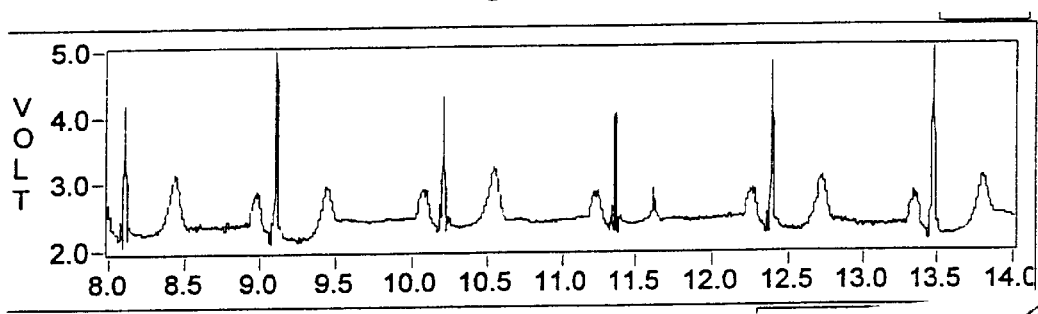
Figure 6C:
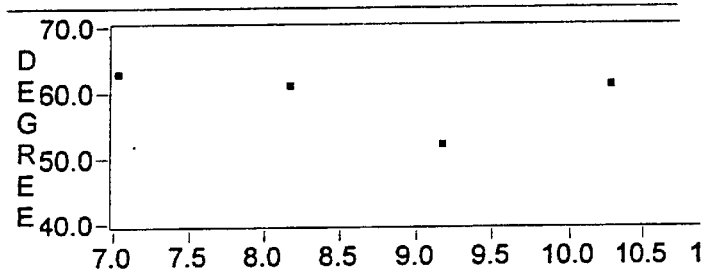
Figure 6D:
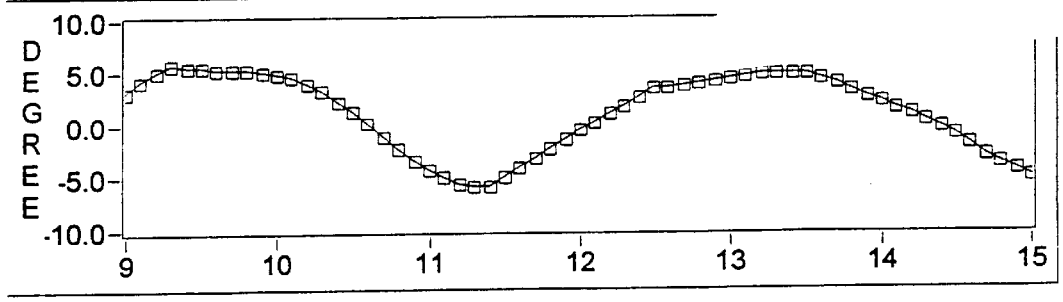

With reference now to FIGS. 6A–6D, data plots for measured and derived data utilizing the process for derivation of respiratory rhythms from ECG signals in accordance with a preferred embodiment of the present invention are depicted. FIGS. 6A and 6B depict data plots of measured ECG signals from leads modified L2 and MCL₁ respectively. FIG. 6C depicts a data plot of computed MEA orientation angles for QRS pulses within the measured ECG signals of FIGS. 6A and 6B. Finally, FIG. 6D depicts a data plot of an EDR signal generated by a cubic spline interpolation of the data points depicted in FIG. 6C.

Figure 7:
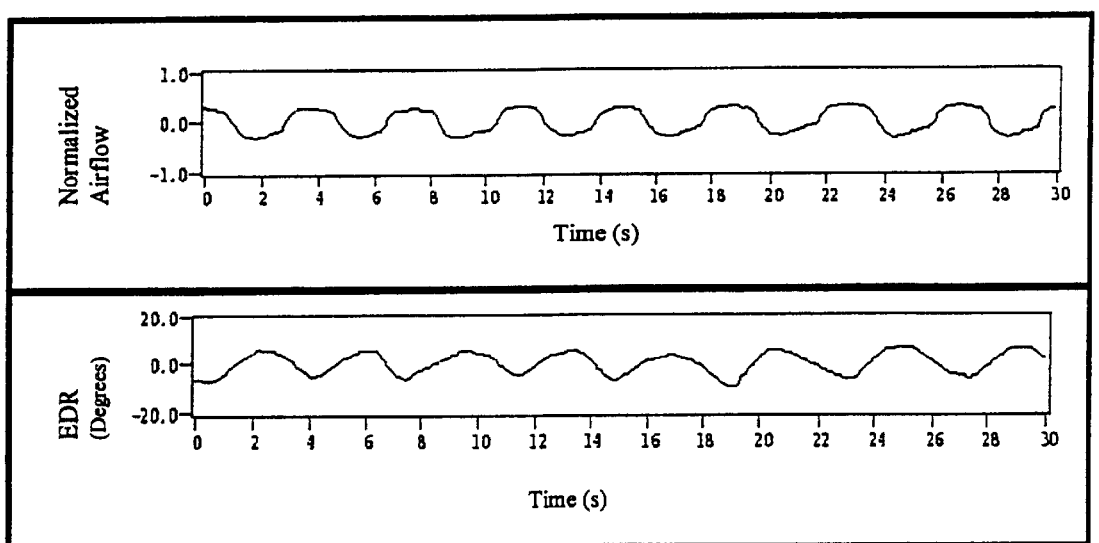
FIG. 7 is a comparative data plot for a measured airflow and a ECG-derived respiratory rhythm signal in accordance with a preferred embodiment of the present invention.
Figure 8:
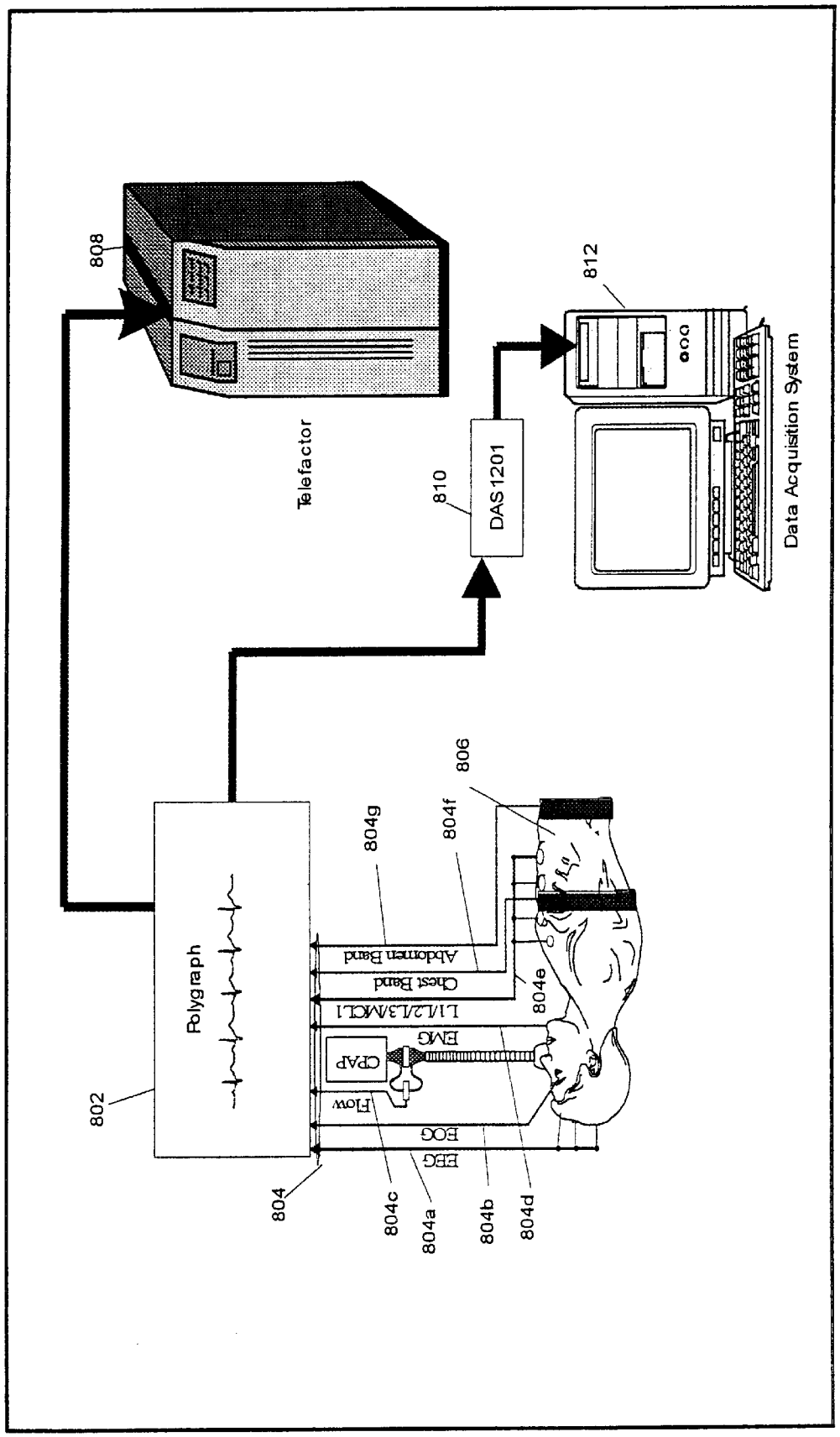
FIG. 8 depicts a conventional arrangement of the polygraphic monitoring instrumentation, in which a preferred embodiment of the present invention may optionally be implemented.

Referring to FIG. 7, a comparative data plot for a measured airflow and a ECG-derived respiratory rhythm signal in accordance with a preferred embodiment of the present invention is illustrated. The present invention may be implemented within a conventional polygraphic monitoring system of the type depicted in FIG. 8. Such an implementation is useful in comparing EDR signals to measured airflow signals to determine how well the EDR signals reflect the lack of air exchange. Subjects may be if asked to simulate obstructive and central apnea prior to the start of a sleep period to provide comparison ECG data when no respiration is present.

It is known that apnea episodes may be associated with large fluctuations in cardiac rates, bradycardia during the apnea, and tachycardia during recovery from an episode in sleep. Increased ventricular ectopy and asystole have also been noted in obstructive sleep apnea patients. Therefore, some positive ECG recordings contain significant cardiac irregularities due to sleep disordered breathing rather than a primary cardiac pathology. Simultaneous examination of measured respiratory data and EDR signals utilizing the present invention within a system of the type depicted in FIG. 8 will allow more accurate identification of sleep-disordered breathing events and permit determination of the cause of positive ECG.

In FIG. 7, measured airflow sampled at 10 Hz and normalized is compared to EDR signals generated for corresponding ECG data. A high correlation is shown between measured airflow patterns and ECG-derived respiratory rhythms, demonstrating the utility of the present invention. ECG data sampled at 500 HZ was processed to generate an EDR signal of respiration sampled at 10 Hz for comparison.

The availability of both measured and derived respiratory data together with cardiac activity data provides the attending cardiologist with the necessary information to discriminated between arrhythmias associated with disordered breathing versus those associated with intrinsic cardiac malfunction. Misdiagnosis of arrhythmias caused by respiratory function can, in extreme cases, lead to expensive and inappropriate treatment such as implanting a heart pacemaker. The present invention may significantly reduce the incidence of such events. No additional equipment, beyond the required data processing software, is required to derive respiratory rhythms from ECG signals. Furthermore, processing may be easily automated and combined with routine processing of extended ECG data with nominal increase in unit costs.

It is important to note that while the present invention has been described in the context of a fully functional electrocardiographic device and/or data processing system, those skilled in the art will appreciate that the mechanism of the present invention is capable of being distributed in the form of a computer readable medium of instructions in a variety of forms, and that the present invention applies equally regardless of the particular type of signal bearing media used to actually carry out the distribution. Examples of computer readable media include: magnetic tape, recordable type media such as floppy disks and CD-ROMs and transmission type media such as digital and analog communication links.

The description of the preferred embodiment of the present invention has been presented for purposes of illustration and description, but is not intended to be exhaustive or limit the invention in the form disclosed. Many modifications and variations will be apparent to those of ordinary skill in the art. The embodiment was chosen and described in order to best explain the principles of the invention and the practical application to enable others of ordinary skill in the art to understand the invention for various embodiments with various modifications as are suited to the particular use contemplated.

What is claimed is:

1. A method for measuring body functions, comprising the following steps:
   (a) placing ECG electrodes on a patient's body in predetermined locations;
   (b) measuring ECG signals in two planes, as a first lead and a second lead;
   (c) locating QRS pulses within measured ECG signals;
   (d) calculating an area of the QRS pulses from measured values of the ECG signals;
   (e) calculating an angle of mean electrical axis; and
   (f) modeling an EDR signal by interpolation between consecutive values of the angle of mean electrical axis.

2. The method for measuring body functions of claim 1, further comprising the step of visually scoring the EDR signal for apneic and hypopneic events.

3. The method for measuring body functions of claim 1, wherein the step of locating QRS pulses in part (c) filter comprises the following steps:
   (a) plotting suitable ECG data representing measurements of an amplitude of the ECG signals in volts as a function of time to form a data plot;
   (b) applying a smoothing filter to the data plot to obtain smoothed data;
   (c) applying a low pass filter to the data plot to obtain low pass filtered data;
   (d) calculating a squared difference between the smoothed data and the low pass filtered data to obtain a squared difference data;
   (e) filtering the squared difference data to obtain a filtered squared difference data; and
   wherein locations of peaks in the filtered squared difference data represent where the QRS pulses are located.

4. The method of measuring body functions of claim 1, wherein the modeling of the EDR signal is performed with a cubic spline interpolation technique.

5. The method of measuring body functions of claim 1, wherein the step of calculating the area of the QRS pulses is by computing a sum of areas of rectangles represented by a sample period and each sample value with a QRS pulse period.

6. The method of measuring body functions of claim 1, wherein the pre-determined locations for electrode placement comprise an intercostal space to the right of a sternum as a V1 electrode, close to an upper left arm as an LA electrode, close to an upper right arm as an RA electrode, and close to a lower left rib as an LL electrode.

7. The method of measuring body functions of claim 1, wherein the step of calculating the angle of mean electrical axis comprises the following steps:
   (a) dividing the area of the QRS pulses as calculated from the ECG signal measurements taken on the first lead by the area of the QRS pulse as calculated from the ECG signal measurements taken on the second lead and obtaining a result; and
   (b) calculating an inverse tangent of the result.

8. The method of measuring body functions of claim 6, wherein the first lead is measured from the RA electrode to the LA electrode and the second lead is measured from the RA electrode to the LL electrode.

9. The method of measuring body functions of claim 6, wherein the first lead is measured from the RA electrode to the LL electrode and the second lead is measured from the LA electrode to the V1 electrode.

10. The method of measuring body functions of claim 9, wherein the RA electrode and the LL electrode comprise using only positive and negative electrodes.

11. The method of measuring body functions of claim 1, further comprising the step of comparing the EDR signals with measured airflow signals in a patient.

12. The method of measuring body functions of claim 1, further comprising measuring additional ECG signals with a conventional polygraphic monitoring system.

13. A method for measuring body functions, comprising the following steps:
   (a) placing ECG electrodes on a patient's body at an intercostal space to the right of a sternum as an V1 electrode, close to an upper left arm as an LA electrode, close to an upper right arm as an RA electrode, and close to a lower left rib as an LL electrode;
   (b) measuring ECG signals in two planes, as a first lead and a second lead;
   (c) locating QRS pulses within measured ECG signals;
   (d) calculating an area of the QRS pulses from measured values of the ECG signals;
   (e) dividing the area of the QRS pulses as calculated from the ECG signal measurements taken on the first lead by the area of the QRS pulse as calculated from the ECG signal measurements taken on the second lead and obtaining a result; then
   (f) calculating an inverse tangent of the result to determine an angle of mean electrical axis;
   (g) modeling an EDR signal by interpolation between consecutive values of the angle of mean electrical axis; and
   (h) visually scoring the EDR signal for apneic and hypopneic events.

14. The method of measuring body functions of claim 13, wherein the first lead is measured from the RA electrode to the LA electrode and the second lead is measured from the RA electrode to the LL electrode.

15. The method of measuring body functions of claim 13, wherein the first lead is measured from the RA electrode to the LL electrode and the second lead is measured from the LA electrode to the V1 electrode.

16. The method of measuring body functions of claim 13, wherein the modeling of the EDR signal is performed with a cubic spline interpolation technique.

17. A method for measuring body functions, comprising the following steps:
   (a) placing ECG electrodes on a patient's body at an intercostal space to the right of a sternum as an V1 electrode, close to an upper left arm as an LA electrode, close to an upper right arm as an RA electrode, and close to a lower left rib as an LL electrode;
   (b) measuring ECG signals in two planes, as a first lead and a second lead;
   (c) locating QRS pulses within measured ECG signals;
   (d) calculating an area of the QRS pulses from measured values of the ECG signals;
   (e) dividing the area of the QRS pulses as calculated from the ECG signal measurements taken on the first lead by the area of the QRS pulse as calculated from the ECG signal measurements taken on the second lead and obtaining a result; then
   (f) calculating an inverse tangent of the result to determine an angle of mean electrical axis;
   (g) modeling an EDR signal by interpolation between consecutive values of the angle of mean electrical axis;
   (h) visually scoring the EDR signal for apneic and hypopneic events; and
   (i) comparing the EDR signals with measured airflow signals in a patient.

18. The method of measuring body functions of claim 17, wherein the first lead is measured from the RA electrode to the LA electrode and the second lead is measured from the RA electrode to the LL electrode.

19. The method of measuring body functions of claim 17, wherein the first lead is measured from the RA electrode to the LL electrode and the second lead is measured from the LA electrode to the V1 electrode.

* * * * *

UNITED STATES PATENT AND TRADEMARK OFFICE
CERTIFICATE OF CORRECTION

PATENT NO. : 6,415,174 B1
DATED : July 2, 2002
INVENTOR(S) : Khosrow Behbehani et al.

It is certified that error appears in the above-identified patent and that said Letters Patent is hereby corrected as shown below:

<u>Title page,</u>
Item [75], Inventors, please correct the first inventor's name "Khosrow Bebhani" to -- Khosrow Behbehani --.

Signed and Sealed this

Thirteenth Day of April, 2004

JON W. DUDAS
*Acting Director of the United States Patent and Trademark Office*